(12) United States Patent
Doyle et al.

(10) Patent No.: US 7,613,571 B2
(45) Date of Patent: Nov. 3, 2009

(54) METHOD AND SYSTEM FOR THE MULTIDIMENSIONAL MORPHOLOGICAL RECONSTRUCTION OF GENOME EXPRESSION ACTIVITY

(76) Inventors: Michael D. Doyle, 726 Irving Ave., Wheaton, IL (US) 60187; Maurice J. Pescitelli, Jr., 5049 Kentwood Dr., Gastonia, NC (US) 28056; Betsey S. Williams, 22 Maple St., Auburndale, MA (US) 02466; George S. Michaels, 14744 Timberbluff Dr., Chesterfield, MO (US) 63017

( * ) Notice: Subject to any disclaimer, the term of this patent is extended or adjusted under 35 U.S.C. 154(b) by 181 days.

(21) Appl. No.: 09/916,709

(22) Filed: Jul. 27, 2001

(65) Prior Publication Data

US 2002/0048766 A1    Apr. 25, 2002

Related U.S. Application Data

(60) Provisional application No. 60/221,611, filed on Jul. 28, 2000.

(51) Int. Cl.
   G01N 33/48    (2006.01)
   G01N 33/50    (2006.01)
(52) U.S. Cl. .............................. 702/19; 435/6; 435/7.1; 703/1
(58) Field of Classification Search .................. 702/19; 435/287.2, 288.4, 7.1
See application file for complete search history.

(56) References Cited

U.S. PATENT DOCUMENTS

| | | | | |
|---|---|---|---|---|
| 5,811,231 | A | * | 9/1998 | Farr et al. ..................... 435/6 |
| 6,058,323 | A | * | 5/2000 | Lemelson ................... 600/408 |
| 6,281,004 | B1 | * | 8/2001 | Bogen et al. ............. 435/287.1 |

OTHER PUBLICATIONS

Cole et al. The genetics of cancer—a 3D model. Nature Genetics Supplement. 1999, vol. 21, pp. 38-41.*
Emmert-Buck et al. Laser Capture Microdissection. Science. 1996, vol. 274, pp. 998-1001.*
Heppelmann et al. Serial sectioning, electron microscopy, and three-dimensional reconstruction of fine nerve fibers and other extended objects. Journal of Microscopy. 1989, vol. 156, Part 2, pp. 163-172.*
"Rasterize" definition, Graphics Software Glossary, 2004, on the world wide web at http://graphicssoft.about.com/od/glossary/l/blrasterize.htm, 2 pages.*
"Aspect" definition, Merriam-Webster online dictionary, 2004, on the world wide web at http://www.m-w.com/cgi-bin/dictionary?book=Dictionary&va=aspect, 2 pages.*
Peter D. Vize, "Online Analysis of Development", BioEssays 23.6, pp. 549-554, copyright 2001, John Wiley & Sons, Inc.

* cited by examiner

Primary Examiner—Carolyn L. Smith
(74) Attorney, Agent, or Firm—Charles E. Krueger

(57) ABSTRACT

A method of morphological reconstruction of biological activity in a tissue sample maps biological data resulting from analysis of tissue samples onto a 3-D morphological rendering of the biological sample. Each slice in a set of histological slices, indexed by a first index, is micro dissected into micro samples indexed by a pair of first and second indices. The indices are utilized to spatially map biological data to the 3-D rendering.

9 Claims, 2 Drawing Sheets

METHOD AND SYSTEM FOR THE MULTIDIMENSIONAL MORPHOLOGICAL RECONSTRUCTION OF GENOME EXPRESSION ACTIVITY

CROSS-REFERENCES TO RELATED APPLICATIONS

This application is a continuation of and claims the benefit of U.S. Provisional Application No. 60/221,611, by Doyle et al. entitled, METHOD AND SYSTEM FOR THE MULTIDIMENSIONAL MORPHOLOGICAL RECONSTRUCTION OF GENOME EXPRESSION ACTIVITY filed Jul. 28, 2000, the disclosure of which is incorporated herein by reference.

BACKGROUND OF THE INVENTION

Genome sequencing

Although biological science finds its roots in a grand tradition of exploratory investigation, for many years, basic research in biology and medicine has focused on a constructionist approach. With the advent of powerful manipulative techniques in molecular biology, most researchers in recent decades have focused on constructing new biological "scenarios" rather than merely observing existing systems. They have done this by perturbing various parameters of otherwise naturally-occurring systems and observing the effect on system dynamics, functional characteristics, etc.

The federally sponsored Human Genome Project (HGP) has recently re-legitimized the exploratory approach for life scientists. The new availability of complete genome sequence information for a variety of species has motivated many large new projects focused entirely on "mining" these data in order to learn more about the basic functions of biological structures and their development through time.

Early progress in the HGP took a directed approach. The federally funded sequencing centers concentrated on the targeted sequencing of specific important genes, working out the gene sequence from start to finish. This approach promised a long and difficult road to completing the entire genome.

Craig Venter, a former NIH researcher, advocated taking a different approach. His idea was rather to take the approach of splitting up the entire genome into small fragments and working on them en masse. This involved dividing the sequencing task among many automatic sequencing machines and attacking the task in parallel, with large numbers of short sequences being determined, and then proceeding to process more batches of the short fragments. Computer scientists then proceeded to reconstruct the fragments' proper order using algorithmic overlap-analysis methods first proposed by Leroy Hood. This method became called "shotgun sequencing" and although persistently derided by the established authorities in the HGP, it proved to be extremely effective in making rapid progress toward the goal of sequencing an entire genome. This work led to the joint announcement on Jun. 26, 2000 by Craig J. Venter, president of Celera Genomics and National Human Genome Research Institute director Francis S. Collins of completion of "the first survey of the entire human genome." The "survey" is the "working draft" of the human genome produced by the publicly funded international consortium HGP and the "first assembly of the human genome" produced by privately funded Celera Genomics.

With the sequencing of the genome nearly complete, the major focus of research is changing. Since gene sequences code for amino acids, the basic building blocks for proteins, many molecular biologists feel that the best place to focus is on creating large libraries of the specific proteins that are coded for by the known genes in the genomic sequence. This field of research is referred to as proteomics [Pandey, A. and M. Mann, Nature, 405(6788):837-46 (2000)]. Other scientists are focused on the task of computational prediction of the 3-dimensional structure of protein molecules directly through analysis of the primary genomic sequences. This area of work is called structural genomics.

Still other scientists, recognizing that the ultimate goal for most life scientists is understanding biological function in normal and diseased states, are focusing more directly on the task of attempting to find specific correlations between gene systems and phenotypic patterns, linking gene sequences directly to clinically-relevant effects. This work is part of what is called functional genomics [Eisenberg, D., et al., Nature, 405(6788):823-6 (2000)]. Functional genomics begins with all available sequence information in pursuit of biological understanding [Lockhart, D. J. and E. A. Winzeler, Nature, 405(6788):827-36 (2000)].

A primary focus of functional genomics is gene expression analysis. This involves the use of a variety of techniques to detect the presence of mRNA sequences within specific tissues. This is done by taking advantage of an effect first observed by Southern, that of the tendency of free nucleotide sequence fragments to hybridize with their complementary mates (see [Southern, E. et al., Nat Genet, 21(1 Suppl):5-9 (1999)] for a recent review). By attaching these sequence fragments to solid supports, and by taking advantage of the binding of various marker molecules to solubilized mRNA, researchers are able to image specific gene expression activity.

cDNA Microarrays

Since that early work, DNA hybridization technology took a tremendous leap forward when the ability was provided to screen a broad spectrum of gene messages at once, through the use of cDNA microarrays [Eisen, M. B. and P. O. Brown, Methods Enzymol, 303:179-205 (1999); Brown, P. O. and D. Botstein, Nat Genet, 21(1 Suppl):33-7 (1999); Cheung, V. G., et al., Nat Genet, 21(1 Suppl):15-9(1999)]. "Gene chips" consist of a solid support to which is attached a regular array of DNA fragments. They are generally created through the use of a robotic system, which coordinates the laying down of a "raster" grid of the DNA probe fragments. The robot deposits this regular grid of pre-determined DNA sequence "spots" onto a fixed substrate, such as a specially-coated glass slide.

These broad-spectrum cDNA chips are organized so that a wide assortment of probes are arrayed in a geometric grid layout, so that the x,y grid coordinate of the grid can be used by a computer system to keep track of which probe is at each location.

The basic steps of a typical microarray analysis is as follows: 1) The tissue to be studied is selected and prepared for RNA extraction. This typically involves homogenization of the tissue to free into solution the desired macromolecules. 2) The mRNA is extracted using standard techniques and then is subjected to reverse transcription in order to produce complementary strands of cDNA molecules. 3) The cDNA molecules are usually synthesized using labeled nucleotides. Use of different labels allows for easy comparison of different mRNA populations. 4) The cDNA probes are then tested by hybridizing them to a DNA microarray. Arrays with more than 250,000 oligonucleotides or 10,000 different cDNAs per square centimeter can now be mass-produced [Lockhart, D. J. and E. A. Winzeler, Nature, 405(6788):827-36 (2000)]. 5) Finally, computer-based image acquisition, processing and analysis is used to quantitate the strength of fluorescent signal at each of the microarray grid locations, thereby providing evidence of the presence and concentration of mRNA corresponding to each of the genes associated with the microarray chip.

Laser Capture Microdissection

Since the gene expression activity of organs and tissues can be quite complex, it is desirable to use a technique which allows analysis of the gene expression, but which permits the morphologic localization of the area to be studied, thus avoiding the loss of morphological detail that results from the homogenization process. Laser capture microdissection (LCM) allows this to be done with great specificity [Bonner, R. F., et al., Science, 278(5342):1481, 1483 (1997); Cole, K. A. et al., Nat Genet, 21(1 Suppl):38-41 (1999); Emmert-Buck, M. R., et al., Science, 274(5289):998-1001 (1996)].

Microdissection-based gene expression analysis begins with the use of a nonaldehyde fixation of the tissue to be studied, using a fixative such as 70% ethanol, since aldehyde fixatives disrupt RNA structure. A low-temperature embedding medium, such as polyethylene glycol distearate, is used to embed the tissue in preparation for histological sectioning. Thin tissue sections are cut, at a thickness of 8 μm, for example, and then are mounted on uncovered glass slides. A thin membrane is typically applied to the section surface to prevent cross-contamination of macromolecules. A UV laser is then used to perform cold ablation of thin lines of tissue, creating an incision around a specific area of the tissue section without disturbing surrounding tissue. A specialized adhesive carrier film is used to transfer the incised portion of the tissue section to an eppendorf microfuge tube with lysis buffer. The cells are lysed in the buffer and can be used for mRNA analysis.

3D localization

The above microdissection technique has been used by Cole, et al. [Cole, K. A. et al., Nat Genet, 21(1 Suppl):38-41 (1999)], to study the cellular-level gene expression activity associated with prostate cancer. These investigators used serial-section histological techniques to precisely identify and then excise specific tumor cells within the prostate gland for microarray analysis of expression activity. The investigators then interactively annotated 3D volume reconstructions of gland section images to overlay expression data relating to the specific cells that had been micro dissected. It should be noted that this study focused on only small groups of specific tissue areas, since the microdissection approach requires a skilled operator and is extremely exacting work. Tissue that isn't used for expression analysis is stained for anatomical reconstruction of the gland architecture, rendering it unusable for further expression analysis. Since this approach is targeted to specific areas of the tissue, it is most useful for specifically targeted studies, and is poorly suited for survey-based exploratory analysis.

Volumetric reconstruction is well known for the macroscopic-level medical imaging techniques of MRI and CT scanning. These 3-dimensional raster-imaging techniques provide useful volumetric surveys for specific anatomical features, but are typically suited for imaging specific sorts of biologic activity. In order to increase the usefulness of these methods, various researchers investigated the combination of multiple imaging modalities, such as MRI and PET scanning, in order to take advantage of the anatomical structure imaging features of the MRI approach, while exploiting the functional data yielded by the PET scanning approach. These multiple datasets are sometimes superimposed upon the same 3-dimensional coordinate space in order to aid in visualization of the functional and structural details.

A similar capability can be provided at a microscopic histological level, through the use of multi-modal imaging of serial microscopic sections for 3D reconstruction and analysis. Alternating serial sections are placed on separate glass slides, with one set of alternating sections stained and coverslipped for histological detail, and the other set of adjacent alternating sections left uncovered for further processing. For each structure seen in a stained coverslipped section, the adjacent section could be easily processed using other techniques. This method is described in detail in Doyle [Doyle, M. D., The intraorgan lymphatic system of the rat left ventricle in normalcy and aging, Univ. of Illinois at Urbana-Champaign, University Microfilms, order number 9210786 (1991)], where it was used to coordinate light microscopic and electron microscopic examination of the three-dimensional aspects of tissue specimens.

Various tools are available for the interactive volume visualization of 3-D biomedical image data. One example is given by the MultiVIS client-server Internet-based distributed visualization system developed by Doyle, et al. [Doyle, M. et al., The Visible Embyro Project: A Platform for Spatial Genomics. in 28th AIPR Workshop: 3D Visualization for Data Exploration and Decision Making (2000); Doyle, M., et al., MultiVIS: A Web-based interactive remote visualization environment and navigable volume imagemap system. in 28th AJPR Workshop: 3D Visualization for Data Exploration and Decision Making (2000)] The MultiVIS system also is a good example of a system which allows for the mapping of both volume image data and other types of data, such as object identity information, onto a single x,y,z coordinate space. This system has been used for a variety of purposes, such as for providing an interactive online 3-D atlas of the Visible Human Project male dataset [Doyle, M., et al., MultiVIS: A Web-based interactive remote visualization environment and navigable volume imagemap system. in 28th AJPR Workshop: 3D Visualization for Data Exploration and Decision Making (2000)]. All the references listed in this paragraph are hereby incorporated by reference for all purposes.

Unsolved problems

Although the above-described existing technologies have enabled numerous advances in biomedical science and industry, there are several long-felt but unsolved needs for which a solution has not been obvious before the present invention. One need is to gather gene expression data in a manner that supports the types of exploratory research that can take advantage of the broad-spectrum types of biologic activity analysis enabled by today's microarray tools. Further, there is a serious need for methods to visualize the spatial distribution of the biologic activity of a wide range of genes, across a wide array of species and tissue types. There is a great need for technology to allow the collection of large volumes of these types of data, to enable exploratory investigations into patterns of biologic activity that may provide insights into both normal and abnormal biologic states. And there is certainly a need to correlate gene expression data with morphological structure in a useful and easy to understand manner, such as in a volume visualization environment.

Each of these needs is evident across all species and ages, however there is a particular need for these problems to be solved in order to enable researchers to make significant progress in the study of early development. Many breakthroughs in biomedical science will only occur through study of organism growth and development. Deciphering the delicate interplay between the spatial expression patterns of various genes and the timings of these biological events is among the most difficult of biomedical research questions. In order to solve such problems, tools are needed to allow the collection of larger volumes of expression data across a wider spectrum of gene types than ever before.

BRIEF SUMMARY OF THE INVENTION

The present invention provides novel and useful methods and systems which help to solve these problems. A new field of work, which is enabled by the present invention, is called "spatial genomics."

According to one aspect of the present invention, a method and system for the multidimensional morphological reconstruction of tissue biological activity makes it possible for a biological tissue specimen to be imaged in multiple dimensions to allow morphological reconstruction. The same tissue specimen is physically sampled in a regular raster array, so that tissue samples are taken in a regular multidimensional matrix pattern across each of the dimensions of the tissue specimen. Each sample is isolated and coded so that it can be later correlated to the specific multidimensional raster array coordinates, thereby providing a correlation with the sample's original pre-sampling morphological location in the tissue specimen. Each tissue sample isolate is then analyzed with broad-spectrum biological activity methods, providing information on a multitude of biologic functional characteristics for that sample. The resultant raster-based biological characteristic data may then be spatially mapped onto the original multidimensional morphological matrix of image data.

According to another aspect of the invention, various types of analysis may then be performed on the resultant correlated multidimensional spatial datasets.

Other features and advantages of the invention will be apparent in view of the following detailed description and appended drawings.

DETAILED DESCRIPTION OF THE INVENTION

Figure 1:
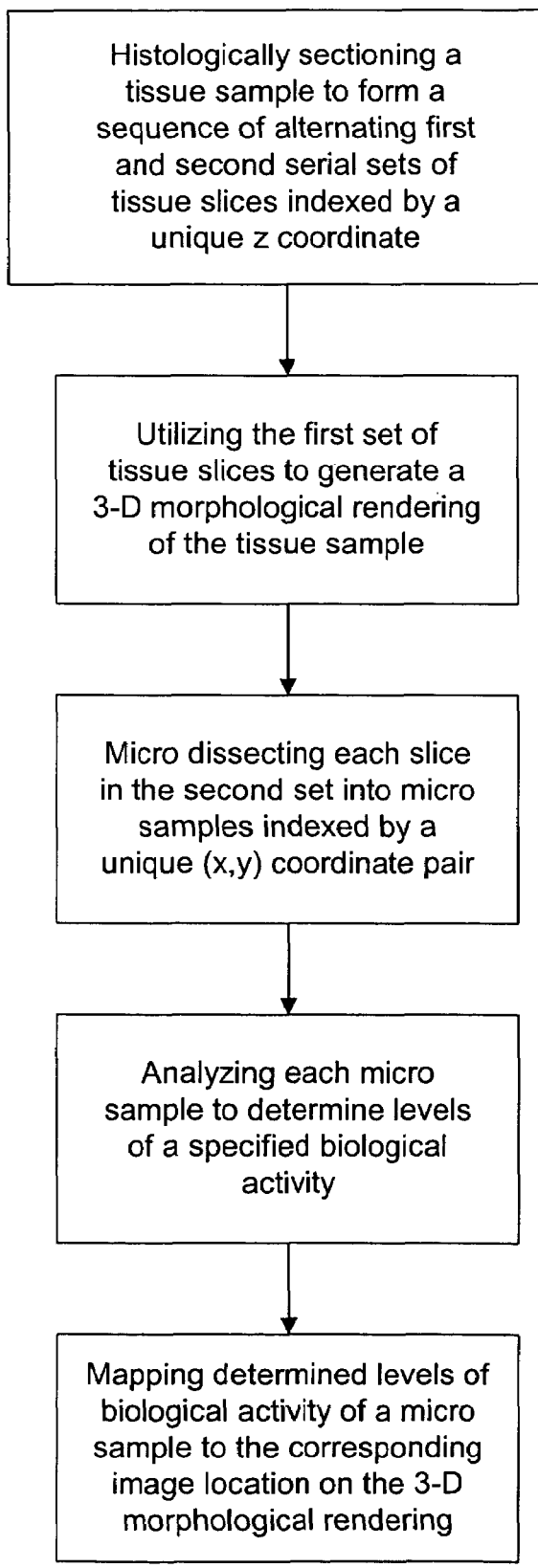
FIG. 1 is a flowchart illustrating a preferred embodiment of the invention.
Figure 2:
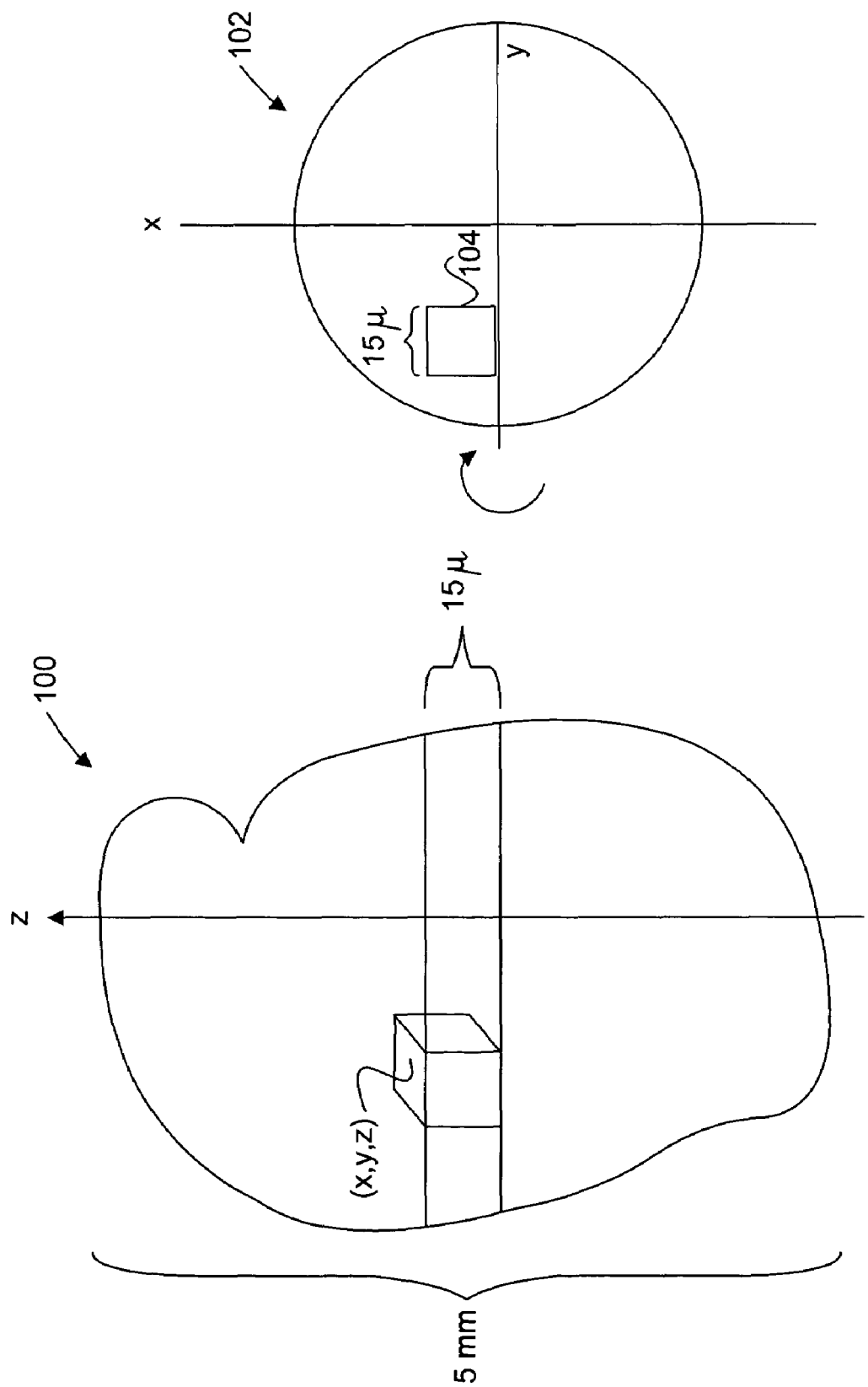
FIG. 2 is a diagram depicting the application of an embodiment of the invention to rasterize embryo tissue.

A specific embodiment of the invention can be used for the study of gene expression analysis as described below.

1) Morphological Imaging

Biological tissue is processed for histological sectioning, using the non-aldehyde fixation method (70% ethanol) and low-temperature embedding medium as described in Cole, et al. [Cole, K. A. et al., Nat Genet, 21(1 Suppl):38-41 (1999)] Histological thin section are then cut, at a thickness of 8 μm, from the embedded tissue, producing two sets of alternating serial sections, as described in Doyle [Doyle, M. D., The intraorgan lymphatic system of the rat left ventricle in normalcy and aging, Univ. of Illinois at Urbana-Champaign, University Microfilms, order number 9210786 (1991)], with one set being histologically-stained for morphological detail and coverslipped for light microscopy. The other set is mounted on glass slides and left unstained with no coverslips, with a microdissection membrane to prevent cross-contamination of macromolecules (see the Molecular-Machines website at extension homepage.php?start=produkte under the heading "micro-manipulation" for detailed protocols).

2) Tissue rasterization

A UV laser of the type described in Cole, et al., [Cole, K. A. et al., Nat Genet, 21(1 Suppl):38-41 (1999)] is used to incise a grid pattern across each tissue section of the uncovered set of alternating serial sections described in #1 above. This is done with the use of said UV laser adapted to the application end of a microarray-creation robotic apparatus, as described in Cheung [Cheung, V. G., et al., Nat Genet, 21(1 Suppl):15-9 (1999)]. This allows for unattended section incising of a large number of specimens. A second adaptation of the robotic apparatus [Cheung, V. G., et al., Nat Genet, 21(1 Suppl):15-9 (1999)] adds a microdissection-transfer film holder to the application end of the apparatus. This transfer film holder is then used to lift each incised section sample from each grid location on each section and transfer each sample to a uniquely-coded isolation tube for lysis and further processing. The sample isolation tubes are arranged in spatial arrays, where each tube is bar coded to indicate the x,y,z tissue-space coordinate of the original pre-sampling morphological matrix location of the sample.

3) RNA amplification

The mRNA can be amplified [Phillips, J. and J. H. Eberwine, Methods, 10(3):283-8 (1996)]. Amplification can also be done using PCR on the cDNA produced by reverse transcription of the mRNA.

4) cDNA Microarray analysis

Each of the mRNA samples is then subjected to DNA microarray analysis [Eisen, M. B. and P. O. Brown, Methods Enzymol, 303:179-205 (1999)]. Reverse transcription is performed on each tissue sample isolate, in order to produce complementary strands of cDNA molecules. The cDNA can be labeled by using labeled nucleotides or the cDNA can be fluorescently labeled. The cDNA probes are then tested by hybridizing them to a DNA microarray. A preferred embodiment uses redundancy of probe locations as an internal control against solution inhomogeneity and other processing variations. Finally, computer-based image acquisition, processing and analysis is used to quantitate the strength of fluorescent signal at each of the microarray grid locations.

5) Spatial Data Mapping

The gene expression data resulting from #4 are then spatially mapped onto the original multidimensional morphological matrix of image data. This is done by setting parameter bits in voxel data, to superimpose the expression message distribution upon the morphological volume image data. The volume image data is correlated with the x, y, z coordinates of the rasterized tissue samples so that the locations of tissue samples are accurately located in the image data. This allows various types of analysis to be performed on the resultant correlated multidimensional spatial datasets. The details of implementing spatial mapping are well-known in the computer arts and not described in detail here.

Some exemplary uses of the spatially mapped data will now be described. A researcher may desire information regarding mRNA synthesis at a particular location, expressed in x, y, z coordinates, of a tissue sample. A 3-dimensional view of the tissue would be displayed on the computer screen allowing the researcher to click on a voxel at the desired location. Techniques for creating an interactive 3-D volume visualization are described in the Multi VIS references described above. For example, as described in the Multi VIS paper, bits in the pixel displayed in the image can store the x,y,z coordinates of the pixel in the multidimensional spatial matrix of image data. These coordinates can be used to access the biological data obtained from analyzing the coded micro dissected sample section indexed by the same x,y,z coordinates. By clicking on a particular part of the image the biological data indexed in those pixels can be accessed. The mRNA synthesis data mapped to the voxel would be displayed in a variety of possible formats, e.g., as a table or a graph.

Alternatively, a researcher may desire information about the expression of a specific gene throughout the tissue sample. In this case, the gene expression data for each voxel is searched to determine whether the specific gene has been expressed. The display is the modified so that the three dimensional image is coded to show the locations where the specific gene is expressed and, optionally, the relative amount of expression.

Most aspects of each of these elements of the invention can be completely automated, thereby allowing for large scale analysis of many tissue specimens.

6) A Specific Example

A specific example illustrating the use and advantages of the above-described techniques will now be described. A human embryo 100 having a length of about 5 mm is micro dissected. The z axis is defined along the dorsal axis and slices of about 8 microns are prepared along the length of the z axis. As described above, alternating sets of serial slices are formed. Each slice from one of the sets is then micros dissected into squares of about 8 microns to rasterize the slice. Thus, voxels 104 in the form of 8 micron cubes are defined, each voxel labelled by its x, y, z coordinates.

The tissue in each voxel is then processed as described above to determine amount of mRNA expression for each tissue sample. This expression data for each voxel is then mapped to the coordinates of each voxel.

ALTERNATIVE EMBODIMENTS

Although the specific embodiment described above focuses on the study of gene expression activity, and uses a specific embodiment suited to that purpose, it will be clear to one with normal skill in the art that other types of biological activity can be studied using the method of the present invention and that many alternative embodiments are possible which conform to the structure and method of the present invention.

Various alternative embodiments of the present invention are possible without changing the fundamental nature of the system. These include, in part: 1) use of a variety of other imaging methods, 2) use of other raster-based sampling methods, 3) use of other ways to isolate tissue samples, 4) use of other types of RNA amplification, such as modified PCR approaches or amplification of the cDNA 5) analysis of other types of biologic activity, such as proteins and other ligands, by monoclonal antibody binding, or any other types of local reactivity that can trigger a visible signal, 6) use of other types of broad spectrum macromolecular hybridization analysis, by microbead columns, for example, and 7) use of a variety of other types of data mapping and analysis.

The invention has now been described with reference to the preferred embodiments. Alternatives and substitutions will now be apparent to persons of skill in the art. For example, the dimensions and particular micro dissection techniques described above are not critical to the invention. Various types of computer systems and languages are suitable for use of the invention and implementation utilizing the Internet would be appropriate. Accordingly, it is not intended to limit the invention except as provided by the appended claims.

What is claimed is:

1. A method for creating a multidimensional morphological reconstruction of biological tissue data characterizing biological tissue comprising the steps of:
    cutting histologically thin sections of said biological tissue to produce first and second sets of alternating serial sections of said biological tissue;
    mapping image data obtained from the first set of alternating serial sections onto a tissue space coordinate system to construct a multidimensional morphological tissue space matrix of image data of the first set of alternating serial sections;
    unattendedly micro dissecting each serial section in the second set of alternating serial sections into a set of micro dissected section samples;
    assigning a unique code to each micro dissected section sample micro dissected from the second set of alternating serial sections to form a set of coded micro dissected section samples, with each unique code indicating tissue space coordinates of each coded micro dissected section sample in the morphological tissue space matrix;
    analyzing each coded micro dissected section sample to obtain biological data providing information on a plurality of biological characteristics of the coded micro dissected section sample; and
    spatially mapping the biological data characterizing each coded micro dissected section sample, micro dissected from the second set of alternating serial sections, onto the multidimensional morphological tissue space matrix, constructed from the first set of alternating serial sections and superimposing the biological data of the coded micro dissected section sample upon volume image data indicated by the code assigned to the coded micro dissected section sample.

2. The method of claim 1 where said step of analyzing comprises the act of:
    analyzing an incised section sample utilizing a monoclonal antibody binding to determine levels of proteins and other ligands.

3. The method of claim 1 where said step of analyzing comprises the act of:
    analyzing a micro dissected section sample with a micro array to determine levels of mRNA.

4. A method for creating a multidimensional morphological reconstruction of gene expression activity in a biological tissue sample comprising the steps of:
    cutting histologically thin sections of said sample to produce first and second sets of alternating serial sample sections;
    histologically-staining and coverslipping said first set of serial sample sections for light microscopy;
    constructing a multidimensional morphological spatial matrix of image data from the first set of histologically-stained serial sample sections;
    mounting and covering the second set of serial sample sections with a micro dissection membrane;
    unattendedly micro dissecting each of the second set of serial sample sections into a plurality of micro dissected section samples;
    providing a set of coded micro dissected section sample holders, with each coded micro dissected section sample holder having a code indicating a unique tissue space coordinate in the multidimensional morphological spatial matrix of image data;
    transferring each micro dissected section sample to a coded micro dissected section sample holder having a code indicating the location of a transferred micro dissected section sample in the multidimensional morphological spatial matrix of image data;
    analyzing each coded micro dissected section sample to obtain biological gene expression data;
    spatially superimposing gene expression data of a micro dissected section sample onto a spatial coordinate of the multidimensional morphological matrix of image data indicated by the code of the coded micro dissected section sample holder holding the micro dissected section sample.

5. The method of claim 4 further comprising the step of:

generating displays correlating values of biological data with locations in the 3-D (three-dimensional) visualization.

6. A method for creating a multidimensional morphological reconstruction of biological data characterizing a biological tissue sample comprising the steps of:

cutting histologically thin sections of said biological tissue sample to form a set of serial sample sections;

constructing a multidimensional morphological spatial matrix of image data from the set of serial sample sections of said biological tissue sample;

unattendedly micro dissecting each serial section of said biological tissue sample into a multidimensional spatial matrix of coded micro dissected section samples, with a code assigned to a coded micro dissected section sample indicating the location of the coded micro dissected section sample in the multidimensional spatial matrix;

analyzing each coded micro dissected section sample to obtain biological data characterizing the coded micro dissected section sample; and linking the biological data characterizing each coded micro dissected section sample to the location in the multidimensional morphological matrix of image data indicated by the code of the coded micro dissected section sample.

7. The method of claim 6 where:

each coded micro dissected section sample analyzed is located in a specific multidimensional volume image data element of the multidimensional morphological spatial matrix of image data from said biological tissue sample, and where each such coded micro dissected section sample contains all of the tissue used to produce said volume image data.

8. The method of claim 6 where:

each coded micro dissected section sample analyzed is located in a specific range of multidimensional volume image data from the multidimensional morphological spatial matrix of image data from said biological tissue sample.

9. A system for creating a multidimensional morphological reconstruction of biological data characterizing a biological tissue sample comprising:

means for cutting histologically thin sections of said biological tissue sample to form a set of serial sample sections;

means for constructing a multidimensional morphological spatial matrix of image data from the set of serial sample sections of said biological tissue sample;

means for unattendedly micro dissecting each serial section of said biological tissue sample into a multidimensional spatial matrix of coded micro dissected section samples, with a code of a coded micro dissected section sample indicating the location of the coded micro dissected section sample in the multidimensional spatial matrix;

means for analyzing each coded micro dissected section sample to obtain biological data characterizing the coded micro dissected section sample; and means for linking the biological data characterizing each coded micro dissected section sample to the location in the multidimensional morphological matrix of image data indicated by the code of the coded micro dissected section sample.

* * * * *

UNITED STATES PATENT AND TRADEMARK OFFICE
CERTIFICATE OF CORRECTION

| | | |
|---|---|---|
| PATENT NO. | : 7,613,571 B2 | Page 1 of 1 |
| APPLICATION NO. | : 09/916709 | |
| DATED | : November 3, 2009 | |
| INVENTOR(S) | : Doyle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 433 days.

Signed and Sealed this

Nineteenth Day of October, 2010

David J. Kappos
*Director of the United States Patent and Trademark Office*